(12) United States Patent
Charlier, Jr. et al.

(10) Patent No.: US 7,727,967 B2
(45) Date of Patent: Jun. 1, 2010

(54) CYANOOXIME INHIBITORS OF CARBONYL REDUCTASE AND METHODS OF USING SAID INHIBITORS IN TREATMENTS INVOLVING ANTHRACYCLINES

(75) Inventors: Henry A. Charlier, Jr., Boise, ID (US); Nikolay Gerasimchuk, Springfield, MO (US)

(73) Assignee: Boise State University, Boise, ID (US)

( * ) Notice: Subject to any disclaimer, the term of this patent is extended or adjusted under 35 U.S.C. 154(b) by 87 days.

(21) Appl. No.: 11/776,536

(22) Filed: Jul. 11, 2007

(65) Prior Publication Data

US 2008/0182804 A1 Jul. 31, 2008

Related U.S. Application Data

(63) Continuation-in-part of application No. 11/711,490, filed on Feb. 26, 2007.

(60) Provisional application No. 60/776,269, filed on Feb. 24, 2006, provisional application No. 60/830,293, filed on Jul. 11, 2006.

(51) Int. Cl.
*A61K 31/70* (2006.01)
*A61K 31/15* (2006.01)
*A01N 43/04* (2006.01)
*A01N 33/24* (2006.01)

(52) U.S. Cl. .......................... 514/34; 514/640

(58) Field of Classification Search ................... 514/34, 514/640
See application file for complete search history.

(56) References Cited

U.S. PATENT DOCUMENTS

| 3,164,524 | A | | 1/1965 | Fand et al. | .................... 167/93 |
| 3,170,945 | A | | 2/1965 | Schisla et al. | ............... 260/463 |
| 3,234,255 | A | * | 2/1966 | Rosinger et al. | ............... 564/47 |
| 3,300,376 | A | | 1/1967 | Schisla et al. | .................. 167/30 |
| 3,336,199 | A | | 8/1967 | Stolar et al. | .................... 167/82 |

FOREIGN PATENT DOCUMENTS

| WO | WO 98/51303 | * | 11/1998 |
| WO | WO 2005/007085 A2 | | 1/2005 |

OTHER PUBLICATIONS

Goodman and Gilman's The Pharmacological Basis of Therapeutics. editors Joel G. Hardman and lee E. Limbird, published by The McGraw-Hill Companies, Inc., 2001, p. 54-56.*
Bacq, et al.; "Successful Treatment of Acute Fascioliasis With Bithionol"*Hepatology* p. 1; 1991.
"Drugs for Parasitic Infections";*The Medical Letter, Inc*; pp. 1-12; Aug. 2004.
Olson, et al.; "Protection from Doxorubicin-Induced Cardiac Toxicity in Mice with a Null Allele of Carbonyl Reductase" *Cancer Research* 63; 6002-6006; Oct. 15, 2003.
Aiken, et al.; "A Cell-Based Screen for Drugs to Treat Huntington's Disease"*Neurobiology of Disease*;16; 546-555; 2004.
Hawn, et al.; "Update on Hepatobiliary and Pulmonary Flukes [Abstract]"*Current Infectious Disease Reports* 1999.
Minotti, et al.; "Anthracyclines: Molecular Advances and Pharmacologic Developments in Antitumor Activity and Cardiotoxicity"; *The American Society for Pharmacology and Experimental Therapeutics*vol. 56, No. 2 185-229; 2004.
Forrest, et al.; "Human Carbonyl Reductase Overexpression in the Heard Adances of the Development of Doxorubicin-induced Cardiotoxicity in Transgenic Mice";*Cancer Research*, 5158-5164; Sep. 15, 2000.
"Bithionol Product Information";*Sigma-Aldrich, Inc*; 2 pages; May 24, 2005.
"2,2'-Sulfinyl-bis (4,6-dichlorophenol) Product Information"; 222. sigmaaldrich.com; May 24, 2005.
Tanaka, et al.; "An Unbiased Cell Morphology -Based Screen for New", Biological Active Small Molecules; *oS Biology*, 0764-0776; May 2005.

* cited by examiner

*Primary Examiner*—Shaojia Anna Jiang
*Assistant Examiner*—Scarlett Goon
(74) *Attorney, Agent, or Firm*—Pedersen & Company, PLLC; Ken J. Pedersen; Barbara S. Pedersen (57) ABSTRACT

Compositions of matter for treating cancer patients are used to prevent or limit cardiotoxicity during or after treatment with anthracycline drugs, and to prevent or lower resistance to anthracycline drugs, both of which are believed to be caused by the human enzyme carbonyl reductase. Preferred embodiments comprise a pharmaceutical composition comprising compounds having halogenated (or pseudo-halogenated) aryl groups, preferably halogenated (or pseudo-halogenated) arylcyanooximes or phenylcyanooximes and derivatives or analogs thereof, including those comprising —CL or —F, or other substituents on an aryl/phenyl ring. The preferred composition of arylcyanooxime(s) may be administered in a pharmaceutical composition also comprising at least one anthracycline compound, or may be administered separately from the at least one anthracycline compound.

2 Claims, 8 Drawing Sheets

**Arrow designates the carbon at position 13

DAUNORUBICINOL

DAUNORUBICIN

| Structure | Compound name |
|---|---|
| C1 | oximino(2,4-difluorophenyl)acetonitrile |
| C2 | oximino(2,6-difluorophenyl)acetonitrile |
| C3 | oximino(2,5-difluorophenyl)acetonitrile |
| C4 | oximino(2-chloro-6-fluorophenyl) acetonitrile |
| C5 | oximino(2,4-dichlorophenyl)acetonitrile |
| C6 | oximino(2,6-dichlorophenyl)acetonitrile |

Fig. 3

X and Y are: F and Cl atoms at the 2,4-; 2,5-; and 2,6-positions (refer to Figures 3A – 3F)

| Inhibitor | $K_{II}$ (μM) | Inhibition Pattern |
|---|---|---|
| C1 | 29 ± 2 | uncompetitive |
| C2 | 51 ± 2 | uncompetitive |
| C3 | 42 ± 1 | uncompetitive |
| C4 | 72 ± 4 | uncompetitive |
| C5 | 11.8 ± 0.7 | uncompetitive |
| C5* | 10.6 ± 0.6 | uncompetitive |
| C6 | 62 ± 4 | uncompetitive |

*This study was performed with a fixed menadione concentration of 250 μM and varied NADPH concentrations ranging from 2 – 50 μM.

CYANOOXIME INHIBITORS OF CARBONYL REDUCTASE AND METHODS OF USING SAID INHIBITORS IN TREATMENTS INVOLVING ANTHRACYCLINES

This application is a continuation-in-part of Ser. No. 11/711,490, filed Feb. 26, 2007 and entitled "Inhibitors Of Carbonyl Reductase For Treatment Using Anthracyclines", which claims priority of Provisional Application No. 60/776,269, filed Feb. 24, 2006. This application also claims priority of Provisional Application No. 60/830,293, filed Jul. 11, 2006, and entitled "Cyanooxime Inhibitors of Carbonyl Reductase and Methods of Using said Inhibitors in Treatments involving Anthracyclines", the entire disclosure of which is hereby incorporated by reference.

Some activities related to this invention were conducted with support by National Institute of Health, NIH/P20RR16454.

BACKGROUND OF THE INVENTION

1. Field of the Invention

This invention relates to compositions of matter, and methods of using said compositions for inhibiting human reductase enzyme(s) that destroy the cell-killing efficacy of anthracycline cancer drugs and that catalyze the formation of dangerous or damaging metabolites during or after cancer treatment. More specifically, embodiments of the invented compositions and methods inhibit human carbonyl reductase, thus inhibiting conversion of anthracycline to metabolites that are less effective cell-killing agents and that also lead to cardiotoxicity during or after treatment of cancer patients. Thus, the invented compositions and methods are believed to lower the amount needed, and the cardiotoxic side-effects, of anthracyclines in cancer treatment.

2. Related Art

Figure 1:
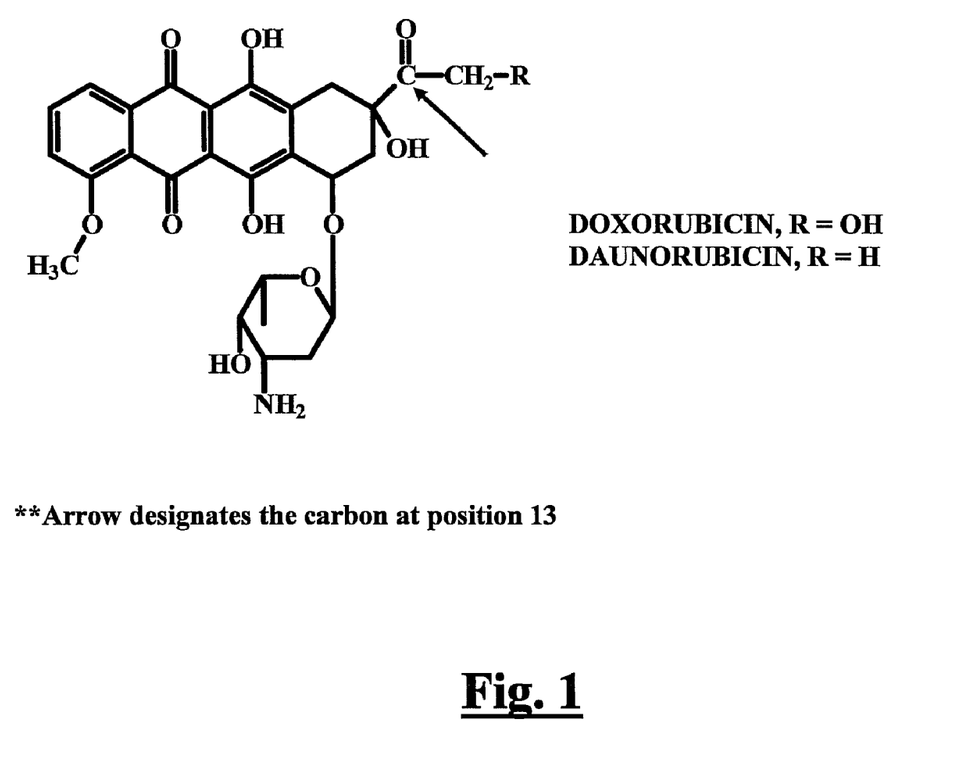
FIG. 1 is a representation of an anthracycline compound, which may be doxorubicin (R=OH) or daunorubicin (R=H), wherein the arrow designates the carbon at position 13.

Anthracyclines are a family of drugs that are effective anti-neoplastic agents, and are commonly used to treat cancer, including leukemia, soft tissue sarcomas, and breast and lung cancer. Anthracyclines intercalate into DNA and are described as topoisomerase Type II poisons. The anthracycline family comprises adriamycin, daunomycin, daunorubicin, doxorubicin, epirubicin, and idarubicin. See, for example, representations of doxorubicin and daunorubicin in FIG. 1.

While the anthracyclines are known to be potent anti-tumor drugs, their use has been limited due to potentially life-threatening cardiotoxicity associated therewith. This problem may be described as cumulative dose-dependent cardiotoxicity, which can ultimately result in congestive heart failure. There is significant evidence that the toxic effects on the heart alcohol metabolite(s) that can form and accumulate in cardiac cells. These metabolites are known to disrupt several key processes in heart muscle and thus impair heart function. See, for example, Minotti, et al., "Anthracyclines: Molecular Advances and Pharmacologic Developments in Antitumor Activity and Cardioitoxicity," *Pharmacological Reviews*, 56: 185-229, 2004.

Enzymes belonging to the aldo-keto reductase and short chain dehydrogenase/reductase protein superfamilies catalyze the formation of the anthracycline metabolites. Of these enzymes, carbonyl reductase ("CR") has been specifically linked to the development of anthracycline-induced cardiotoxicity. See, for example, Olson, et al., "Protection from Doxorubicin-Induced Cardiac Toxicity in Mice with a Null Allele of Carbonyl Reductase 1," *Cancer Research*, 63, 6602-6606, Oct. 15, 2003. Findings that support the hypothesis that CR is a key factor in anthracycline-induced cardiotoxicity include studies wherein heart-specific over-expression of human carbonyl reductase in transgenic mice substantially increased the development of cardiotoxicity after anthracycline treatment. See, for example, Forrest, et al., "Human Carbonyl Reductase Overexpression in the Heart Advances the Development of Doxorubicin-induced Cardiotoxicity in Transgenic Mice," *Cancer Research*, 60, 5158-5164, Sep. 15, 2000.

Further, several studies have implicated the reduction of anthracyclines by carbonyl reductase in drug resistance. This is largely because the alcohol metabolites of anthracyclines have been shown to exhibit significantly lowered anticancer properties. Relevant to this are studies performed by Tanaka, et al., (reported in Tanaka, et al., "An Unbiased Cell Morphology-Based Screen for New, Biologically Active Small Molecules," PLoS Biology, Vol. 3, Iss. 5, 0764-0776, May 2005). Tanaka, et al. report that a potent inhibitor of human carbonyl reductase (3-(7-isopropyl-4-(methylamino)-7H-pyrrolo[2,3-d]pyrimidin-5-yl)phenol, when coadministered with daunorubicin to A549 adenocarcinoma cells, was found to enhance the cytotoxicity of daunorubicin. It was concluded that inhibition of carbonyl reductase led to enhanced cytotoxicity of daunorubicin.

Figure 2:
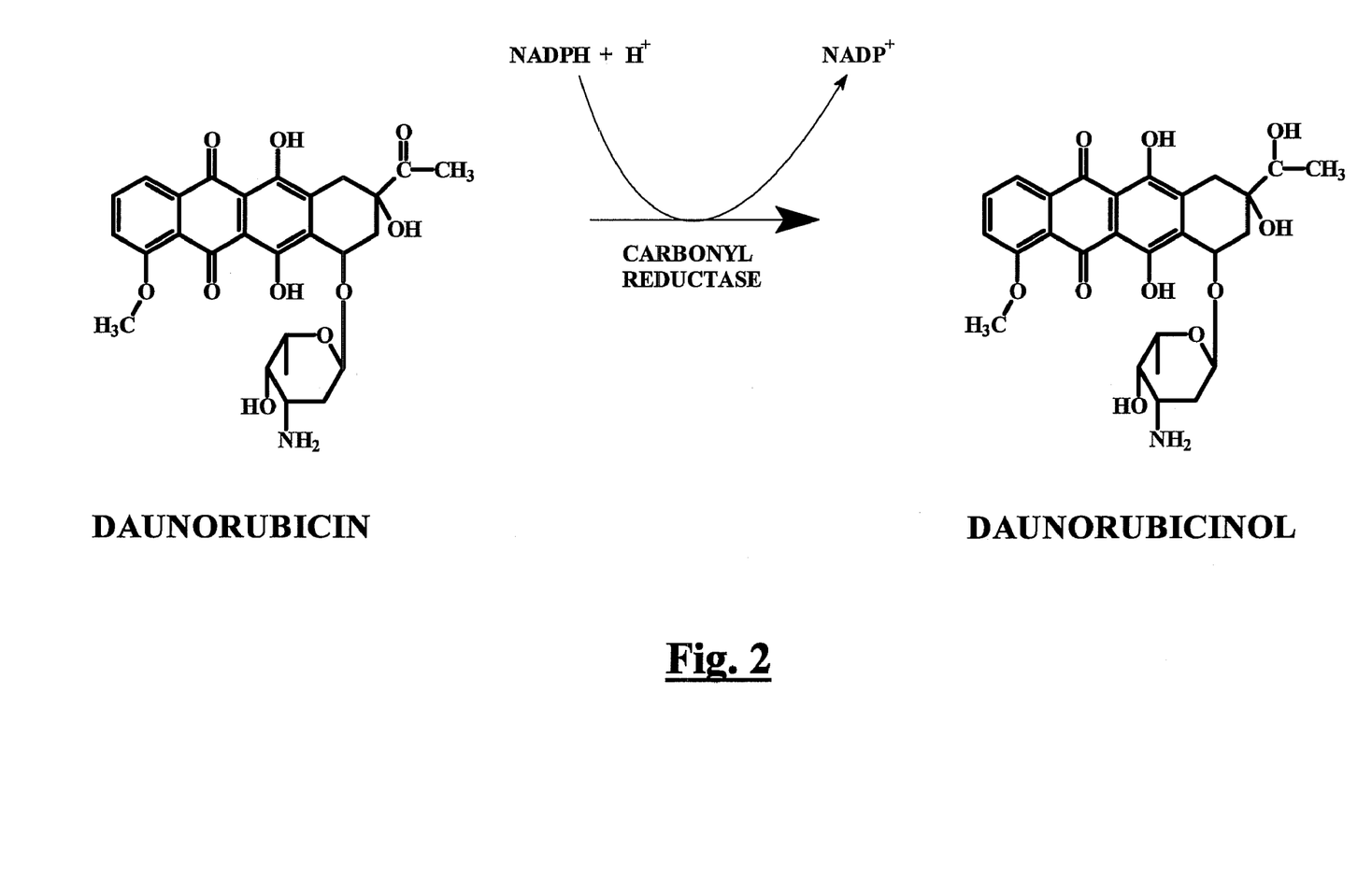
FIG. 2 is a representation of a carbonyl reductase-NADPH mechanism for reducing the anthracycline daunorubicin to the anthracycline alcohol metabolite daunorubicinol.
Figure 3:
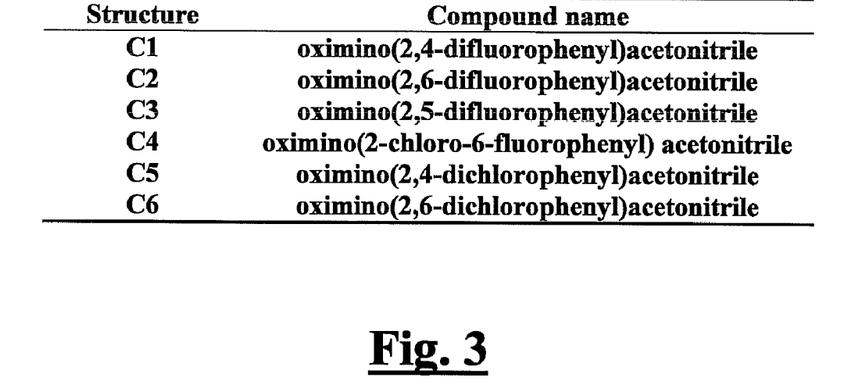
FIGS. 3A-F show the chemical structures of oximino(2,4-difluorophenyl)acetonitrile (C1, in FIG. 3A); oximino(2,6-difluorophenyl)acetonitrile (C2, in FIG. 3B); oximino(2,5-difluorophenyl)acetonitrile (C3, in FIG. 3C); oximino(2-chloro-6-fluorophenyl)acetonitrile (C4, in FIG. 3D); oximino(2,4-dichlorophenyl)acetonitrile (C5, in FIG. 3E); oximino(2,6-dichlorophenyl)acetonitrile (C6, in FIG. 3F).
Figure 3A:
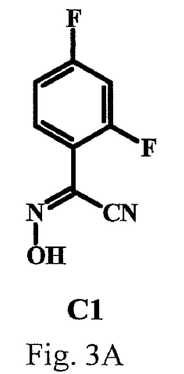
Figure 3B:
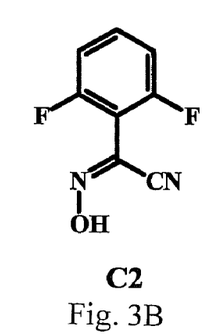
Figure 3C:
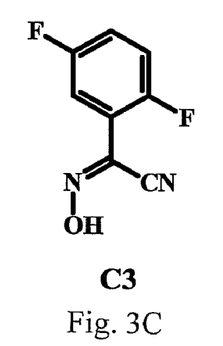
Figure 3D:
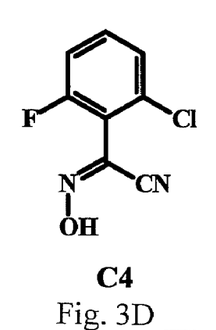
Figure 3E:
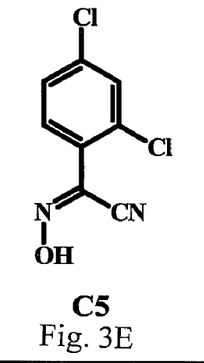
Figure 3F:
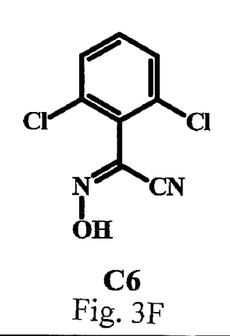

See, for example, the FIG. 2 representation of carbonyl reductase catalysis (reduction via NADPH+$H^+$ mechanism) of the anthracycline daunorubicin to daunorubicinol. While daunorubicin is an effective anti-cancer agent by means of its effective disruption of DNA replication, daunorubicinol exhibits reduced anti-cancer properties and is a potent cardiotoxin. Therefore, conversion to the alcohol metabolite not only creates a potent cardiotoxin, but also lowers the efficacy of the treatment for a given amount of anthracycline.

Therefore, the inventor believes that there is a need for pharmaceutical interventions that block the action of human carbonyl reductase. The inventor believes that such pharmaceutical interventions will increase the efficacy of anthracycline therapy in cancer/tumor treatment by preventing or lowering conversion of anthracyclines to less potent cell-killing species and by reducing the risk of cardiotoxicity.

SUMMARY OF THE INVENTION

The present invention comprises compositions of matter, and methods of treating patients with the compositions of matter, to prevent or lower conversion in the human body of anthracycline drugs to metabolites that are less effective for cancer treatment and that are also believed to produce cardiotoxicity during or after cancer treatment. Hence, by using embodiments of the invented compositions and/or methods, the effectiveness of a given dose of anthracycline drugs may increase and the risk of cardiotoxicity typically associated with said treatment may lessen.

Embodiments of the invention comprise inhibiting carbonyl reductase enzyme(s) and/or other enzyme(s) that catalyze anthracycline conversion to anthracycline metabolites. This has the direct effect of maintaining concentrations of anthracyclines, which are desirable for their cell-killing abilities, and, hence, for their cancer-cell-killing abilities. This inhibition also has the indirect effect of lowering formation of metabolites that build up during or after treatment with anthracycline cancer drugs, said metabolites being ones that are believed to disrupt heart muscle processes and therefore to interfere with heart function. Therefore, by using embodiments of the invented compositions and/or methods, much less anthracycline drug is expected to be needed to achieve the desired killing of cells, and much less cardiotoxic metabolite will be produced over the duration of the cancer treatment.

The invented compositions comprise compounds having at least one aryl group (preferably at least one phenyl group), wherein at least one of said at least one aryl/phenyl group comprises halogen or pseudo-halogen. In the preferred embodiments disclosed herein, these halogenated (or pseudo-halogenated) aryl/phenyl compounds further comprise at least one cyanooxime group. Especially-preferred embodiments of the invention comprise one or more disubstituted arylcyanooximes (or use thereof), and preferably at least one of the following compounds: oximino(2,4-difluorophenyl)acetonitrile (herein referred to as "C1") and/or oximino(2,6-difluorophenyl)acetonitrile (herein referred to as "C2") and/or oximino(2,5-difluorophenyl)acetonitrile (herein referred to as "C3") and/or oximino(2-chloro-6-fluorophenyl)acetonitrile (herein referred to as "C4") and/or oximino(2,4-dichlorophenyl)acetonitrile (herein referred to as "C5") and/or oximino(2,6-dichlorophenyl)acetonitrile (herein referred to as "C6") and/or derivatives or analogs thereof. The preferred composition of C1, C2, C3, C4, C5, and/or C6, and/or derivatives or analogs thereof, may be administered to a human (or other mammal) in a pharmaceutical composition also comprising at least one anthracycline compound, or may be administered separately from the at least one anthracycline compound either at the same time as the anthracycline(s), or any different time found to be effective for inhibiting formation of the anthracycline metabolites.

Therefore, an object of the present invention is to inhibit one or more of the members of the aldo-keto reductase and/or short chain dehydrogenase/reductase protein superfamilies, which catalyze the conversion of anthracyclines to anthracycline metabolites. The preferred compositions and methods are adapted to inhibit member(s) of these superfamilies, currently associated with cardiotoxicity from anthracycline chemotherapy, that is, human carbonyl reductase. A synergistic effect of inhibiting said reductase enzyme is expected to be that lower dosages of the anthracycline drug will be effective for cancer-cell-killing.

A method for synthesizing disubstituted arylcyanooximes, including C1, C2, C3, C4, C5, and C6 is also disclosed. Such compounds can be synthesized by nitrosating the appropriate disubstituted phenylacetonitriles by treatment with neat organic nitrites.

DESCRIPTION OF THE PREFERRED EMBODIMENTS

Referring to the figures, there are shown several, but not the only, embodiments of the invented composition of matter and methods for enhancing the efficacy of anthracycline drug cancer treatment and/or limiting side-effects thereof. The preferred methods and compositions of matter may maintain effective concentrations of anthracycline(s) during cancer treatment, by preventing or lowering conversion of the anthracycline(s) to metabolites that are less effective or ineffective as cancer-cell-killing species. The preferred methods and compositions may also prevent or lower the potentially life-threatening cardiotoxicity associated with anthracycline chemotherapy for cancer patients.

The preferred compounds, for use in the above-described prevention or lowering of anthracycline conversion, have at least one aryl (preferably phenyl) group, wherein at least one aryl/phenyl group comprises halogen or pseudo-halogen. Pseudo-halogens may include binary inorganic compounds of the general form XY, where X is a cyanide, cyanate, or thiocyanate and where Y is any of X or a true halogen, including but not limited to cyanogen ($(CN)_2$) and iodine cyanide (ICN). Preferably, these halogenated (or pseudo-halogenated) aryl/phenyl compounds further comprise at least one cyanooxime group. The especially-preferred embodiments comprise one or more disubstituted arylcyanooximes, and preferably one or more of the following compounds: oximino(2,4-difluorophenyl)acetonitrile (herein referred to as "C1"), oximino(2,6-difluorophenyl)acetonitrile (herein referred to as "C2"), oximino(2,5-difluorophenyl)acetonitrile (herein referred to as "C3"), oximino(2-chloro-6-fluorophenyl)acetonitrile (herein referred to as "C4"), oximino(2,4-dichlorophenyl)acetonitrile (herein referred to as "C5"), or oximino(2,6-dichlorophenyl)acetonitrile (herein referred to as "C6"). See FIGS. 3A-F. Also, it is expected that derivatives or analogs of these compounds may be effective in the place of one or more of these six compounds, or as a supplement to one or more of these compounds.

Figure 4:
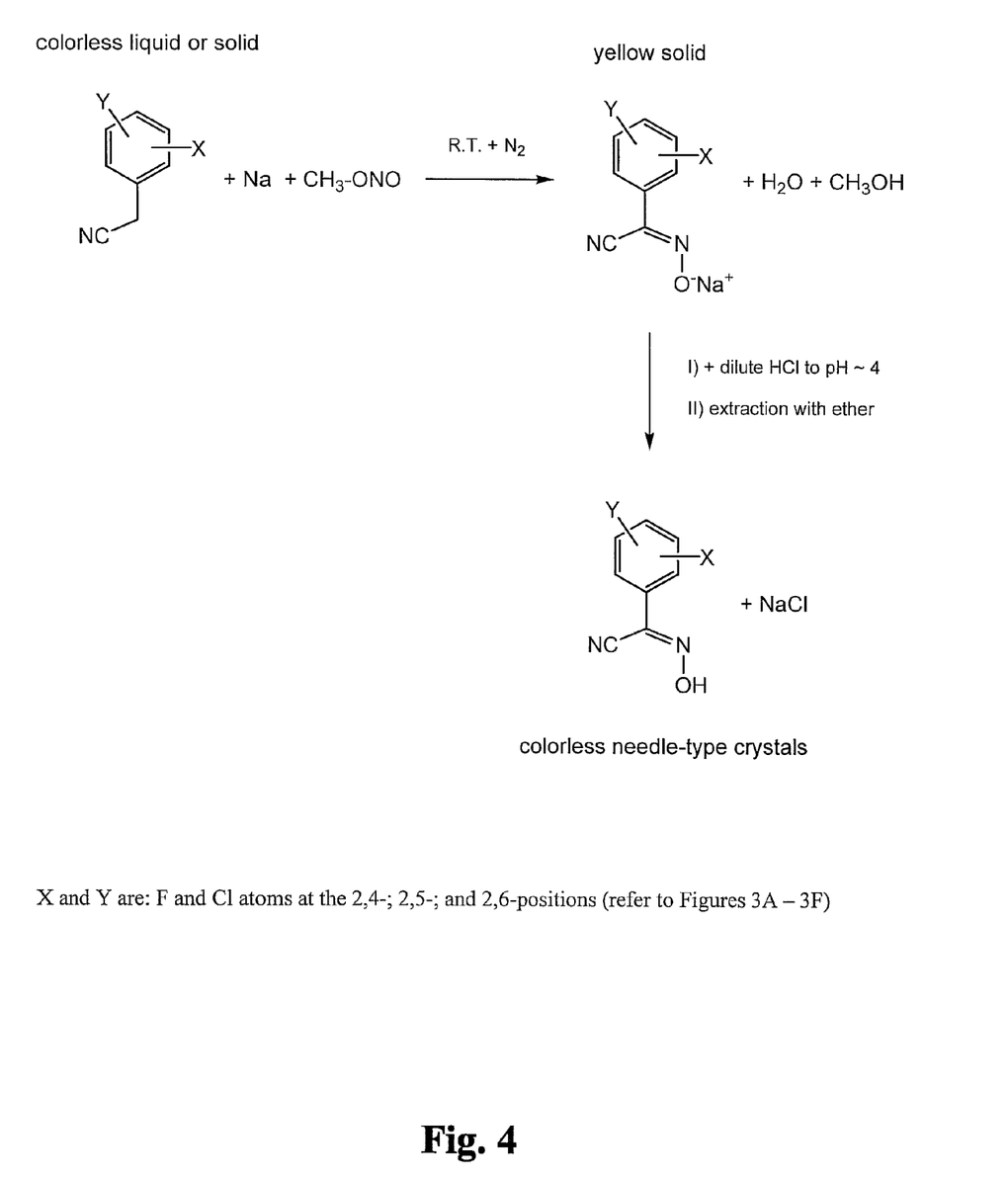
FIG. 4 shows a scheme describing the general synthetic strategy used to create C1, C2, C3, C4, C5, and C6, wherein X and Y may be F and Cl atoms at the 2,4-; the 2,5-; and the 2,6-positions (as will be understood by viewing FIGS. 3A-F), and wherein R—ONO refers to alkylnitrites.

The general synthetic strategy used to make compounds C1, C2, C3, C4, C5, and C6 is outlined in FIG. 4. Commercially-available alkylnitrites were found to lack stability, and so were less than optimal for the desired synthesis. Instead, an improved synthesis has been invented that comprises the use of gaseous methylnitrite, $CH_3$—ONO, as a nitrosating agent. Small quantities (2-5 L) of the gaseous methylnitrite were made fresh before each use, from $NaNO_2$, $CH_3OH$, and $H_2SO_4$. This invented technique resulted in very high yields of the desired oxime. The typical procedure for the synthesis of the preferred dihalogenated arylcyanooximes is presented below:

Synthesis of oximino(2,4-difluorophenyl)acetonitrile, ("C1")

Thinly sliced metallic sodium (0.754 g; 0.033 mol) was dissolved at room temperature and under $N_2$ protection in 300 mL of i-propanol. The starting 2,4-difluorophenyl-acetonitrile, $NC-CH_2-C_6H_3F_2$ (5.000 g; 0.033 mol), was dissolved in 50.0 mL of i-propanol and then added to the sodium isopropoxide solution. Freshly-obtained (within about 10 minutes) from $NaNO_2$, $CH_3OH$, and $H_2SO_4$, gaseous methylnitrite $CH_3-ONO$ was bubbled slowly at room temperature through the mixture of $NaOC_3H_7$ and $NC-CH_2-C_6H_3F_2$ in i-propanol for 30 minutes. Color of the reaction mixture immediately turned yellow. After an overnight standing at ~4° C., the solvent was removed using the rotovap and the remaining yellow solid residue of NaL (L=2,6-diF-PhCO) was thoroughly dried at room temperature using an oil pump. The solid NaL was re-dissolved in 50 mL of water and the solution was slowly acidified with 1.0M HCl. At pH ~7 white precipitate started to appear in the flask. The precipitate of HL was filtered, washed with water and dried in vacuum desiccator resulting in 5.13 g (0.029 mol) of the cyanooxime at 86% yield. M.p.=64–65° C., $R_f$=0.37 in EtOAc:hexane=1:4 mobile phase. Found: C, 52.80; H, 2.24; N, 15.47. $C_8H_4F_2N_2O$ requires: C, 52.76; H, 2.21; N, 15.38. NMR spectra evidenced the mixture of syn (60%) and anti (40%) isomers in DMSO-$d_6$. Data for syn-isomer: $^1H$ NMR, ppm: 14.12 (1H, s, oxime group); 7.75 (1H, multiplet at 6-position; $^3J_{(^1H-^1H)}$=8.0 Hz, $^5J_{(^1H-^1H)}$=2.0 Hz, $^4J_{(^1H-^{19}F)}$=80.5 Hz); 7.47 (1H, multiplet at 5-position; $^3J_{(^1H-^1H)}$=8.5 Hz, $^4J_{(^1H-^1H)}$=2.5 Hz, $^3J_{(^1H-^{19}F)}$=11.5 Hz, $^5J_{(^1H-^{19}F)}$=3.0 Hz); 7.25 (1H, multiplet at 3-position; $^3J_{(^1H-^1H)}$=8.0 Hz, $^4J_{(^1H-^{19}F)}$=6.5 Hz). $^{13}C$ NMR, ppm.: 163.87—carbon at 2-position, ($^1J_{(^{13}C-^{19}F)}$=251 Hz, $^3J_{(^{13}C-^{19}F)}$=12.3 Hz), 159.82—carbon at 4-position ($^1J_{(^{13}C-^{19}F)}$=255 Hz, $^3J_{(^{13}C-^{19}F)}$=12.8 Hz), 131.09—carbon at 6-position ($^3J_{(^{13}C-^{19}F)}$=10.4 Hz, $^3J_{(^{13}C-^{19}F)}$=4.0 Hz), 126.31—oxime carbon, 113.17—ipso-carbon ($^2J_{(^{13}C-^{19}F)}$=220.0 Hz, $^4J_{(^{13}C-^{19}F)}$=3.3 Hz), 110.28—CN-group, 105.82—carbon at 3-position ($^2J_{(^{13}C-^{19}F)}$=25.9 Hz), 105.62—carbon at 5-position ($^2J_{(^{13}C-^{19}F)}$=250.1 Hz, $^4J_{(^{13}C-^{19}F)}$=2.0 Hz). UV-visible spectrum, $\lambda_{max}$ (EtOH)/nm, $\epsilon$/(dm$^3$ M$^{-1}$ cm$^{-1}$): 261 (6200). IR data, cm$^{-1}$: 3296ν(O—H); 3115ν(C—H); 2238ν(C≡N); 1613, 1595ν(C=C); 1505ν(C=C) Ph-group pulsing; 822, 855, 866δ(C—H) 1,2,4-Ph-group pattern; 1446, 1426ν(C=N); 1057, 983ν(N—O); 1270$^{as}$, 1104$^s$ν(C—F).

Syntheses of the other cyanooximes followed similar procedures with the appropriate corresponding phenylacetonitrile. The characterization of the resulting products follow:

Oximino(2,6-difluorophenyl)acetonitrile, ("C2")

Colorless crystalline substance; M.p.=99–100° C., $R_f$=0.29 (EtOAc:hexane=1:4). Found: C, 52.71; H, 2.18; N, 15.43. $C_8H_4F_2N_2O$ requires: C, 52.76; H, 2.21; N, 15.38. NMR spectra evidenced the mixture of syn (~50%) and anti (~50%) isomers. Data for syn-isomer: $^1H$ NMR, ppm: 14.46 (1H, s, oxime group); 7.68 (1H, ten lines multiplet); 7.30 (2H, seven lines multiplet); $^{13}C$ NMR, ppm.: 160.00 (carbon at 2-position; $^1J_{(^{13}C-^{19}F)}$=254 Hz, $^3J_{(^{13}C-^{19}F)}$=5.1 Hz), 112.74 (carbon at 3-position; $^2J_{(^{13}C-^{19}F)}$=20.5 Hz, $^4J_{(^{13}C-^{19}F)}$=4.3 Hz), 110.01 (carbon at 4-position), 134.05 (ipso carbon; $^2J_{(^{13}C-^{19}F)}$=10.8 Hz), 123.91 (oxime carbon), 105.62 (CN group). Mass-spectrometry: for $C_8H_4F_2N_2O$ found (required)—182.0299 (182.0292). UV-visible spectrum, $\lambda_{max}$ (EtOH)/nm, $\epsilon$/(dm$^3$ M$^{-1}$ cm$^{-1}$): 210 (5900), 244 (5550). IR data, cm$^{-1}$: 3224ν(O—H); 3115, 3083ν(C—H); 2254, 2238ν(C≡N); 1623, 1602ν(C=C); 1475ν(C=C)-Ph-group pulsing; 725, 748, 771, 791δ(C—H)—1,2,3-Ph-group pattern; 1411, 1426ν(C=N); 1160, 1004, 981ν(N—O); 1275$^{as}$, 1239$^s$ν(C—F). X-ray quality needle like crystals of this cyanooxime were obtained by slow evaporation of its aqueous solution.

Oximino(2,5-difluorophenyl)acetonitrile, ("C3")

Colorless needle-type crystals; yield=91%, m.p.=64–67° C., $R_f$=0.24 (EtOAc:hexane=1:4). Found: C, 52.80; H, 2.26; N, 15.47. $C_8H_4F_2N_2O$ requires: C, 52.76; H, 2.21; N, 15.38. Only one isomer (syn) in solutions. $^1H$ NMR, ppm: 14.29 (1H, s, oxime group); 7.49 (1H, multiplet, ddd); 7.45 m (2H, multiplet, ddd). $^{13}C$ NMR, ppm.: 158.39—carbon at 2-position ($^1J_{(^{13}C-^{19}F)}$=242 Hz, $^4J_{(^{13}C-^{19}F)}$=2.1 Hz), 155.69—carbon at 5-position ($^1J_{(^{13}C-^{19}F)}$=248 Hz, $^4J_{(^{13}C-^{19}F)}$=2.3 Hz), 126.12—oxime carbon, 119.82—carbon at 3-position ($^2J_{(^{13}C-^{19}F)}$=24.3 Hz, $^3J_{(^{13}C-^{19}F)}$=8.9 Hz), 119.41—ipso-carbon ($^2J_{(^{13}C-^{19}F)}$=12.9 Hz, $^3J_{(^{13}C-^{19}F)}$=8.2 Hz), 118.96—carbon at 4-position ($^2J_{(^{13}C-^{19}F)}$=22.8 Hz, $^3J_{(^{13}C-^{19}F)}$=8.2 Hz), 115.34—carbon at 6-position ($^2J_{(^{13}C-^{19}F)}$=26.5 Hz, $^3J_{(^{13}C-^{19}F)}$=2.5 Hz), 110.06—CN-group. UV-visible spectrum, $\lambda_{max}$ (EtOH)/nm, $\epsilon$/(dm$^3$ M$^{-1}$ cm$^{-1}$): 204 nm ($\epsilon$=16080 dm$^3$ M$^{-1}$ cm$^{-1}$), 259 (7320). IR data, cm$^{-1}$: 3350ν(O—H); 3127, 3087ν(C—H); 2246ν(C≡N); 1439, 1411ν(C=C); 1495ν(C=C) Ph-group pulsing; 773, 835, 844δ(C—H) 1,2,5-Ph-group pattern; 1283ν(C=N); 1073, 1009ν(N—O); 1252$^{as}$, 1193$^s$ν(C—F). X-ray quality needle-like crystals were obtained by slow cooling in thermostat hot solution of compound in $CCl_4$.

Oximino(2-chloro-6-fluorophenyl)acetonitrile, ("C4")

Colorless needles; yield 45%, m.p.=119–120° C., $R_f$=0.38 (EtOAc:hexane=1:4). Found: C, 48.33; H, 2.09; N, 14.23. $C_8H_4ClN_2O$ requires: C, 48.39; H, 2.03; N, 14.11. NMR spectra indicate mixture of syn (73%) and anti (27%) isomers in DMSO-$d_6$. The following data for syn-isomer. $^1H$ NMR, ppm: 14.51 (1H, s, oxime group); 7.66 (1H, multiplet at 5-position; $^3J_{(^1H-^1H)}$=8.5 Hz, $^3J_{(^1H-^{19}F)}$=8.51 Hz); 7.53 (1H, doublet at 3-position; $^3J_{(^1H-^1H)}$=8.5 Hz); 7.45 (1H, multiplet at 4-position; $^3J_{(^1H-^1H)}$=7.5 Hz, $^4J_{(^1H-^{19}F)}$=1.0 Hz). $^{13}C$ NMR, ppm.: 159.31—carbon at 6-position ($^1J_{(^{13}C-^{19}F)}$=251 Hz), 134.07—carbon at 4-position ($^3J_{(^{13}C-^{19}F)}$=9.6 Hz), 132.79—carbon at 2-position ($^3J_{(^{13}C-^{19}F)}$=4.6 Hz), 126.32—carbon at 3-position ($^4J_{(^{13}C-^{19}F)}$=3.0 Hz), 126.26—oxime carbon, 116.32—carbon at 1-position ($^2J_{(^{13}C-^{19}F)}$=20.7 Hz), 115.85—carbon at 5-position ($^2J_{(^{13}C-^{19}F)}$=21.3 Hz), 114.72—CN-group. UV-visible spectrums, $\lambda_{max}$ (EtOH)/nm, shoulders at 214 and 261 nm. IR data, cm$^{-1}$: 3330ν(O—H); 3099, 3080ν(C—H); 2246ν(C≡N); 1610, 1600, 1577ν(C=C); 1451ν(C=C) Ph-group pulsing; 727, 760, 792δ(C—H) 1,2,3-Ph-group pattern; 1467, 1408ν(C=N); 1052, 1032ν(N—O); 1252ν(C—F); 1085ν(C—Cl). X-ray quality needle-type single crystals of this compound were obtained from $CHCl_3$.

Oximino(2,4-dichlorophenyl)acetonitrile, ("C5")

Colorless fibrous crystalline substance; yield 95%, m.p.=151° C., $R_f$=0.34 (EtOAc:hexane=1:4). Found: C, 44.71; H, 1.98; N, 13.23. $C_8H_4Cl_2N_2O$ requires: C, 44.68; H, 1.87; N, 13.03. NMR spectra show mixture of anti (70%) and syn (30%) isomers in DMSO-$d_6$. Presented data for anti-isomer. $^1H$ NMR, ppm: 14.24 (1H, s, oxime group), 7.82 (1H, s, at 3-position), 7.66 (1H, multiplet, at 5-position), 7.58 (1H, at 6-position). $^{13}$C NMR, ppm.: 136.71—carbon at 2-position, 132.92—carbon at 3-position, 132.45—carbon at 4-position, 130.36—carbon at 5-position, 128.64—carbon at 6-position, 127.70—oxime carbon, 110.13—CN-group. UV-visible spectrum, $\lambda_{max}$ (EtOH)/nm, $\epsilon/(dm^3\ M^{-1}\ cm^{-1})$: 225 nm shoulder, 265 nm ($\epsilon$=11200 $dm^3\ M^{-1}\ cm^{-1}$). IR data, $cm^{-1}$: 3340$\nu$(O—H); 3087$\nu$(C—H); 2194$\nu$(C≡N); 1631, 1587$\nu$(C═C); 1475$\nu$(C═C) Ph-group pulsing; 812, 830, 871$\delta$(C—H) 1,2,4-Ph-group pattern; 1405$\nu$(C═N); 1050$\nu$(N—O); 1104$^{as}$, 1070$^s\nu$(C—Cl).

Oximino(2,6-dichlorophenyl)acetonitrile, ("C6")

Colorless microcrystalline substance; yield 60%, m.p.=94-96° C., $R_f$=0.29 (EtOAc:hexane=1:4). Found: C, 44.75; H, 1.94; N, 13.12. $C_8H_4Cl_2N_2O$ requires: C, 44.68; H, 1.87; N, 13.03. NMR spectra evidenced the mixture of syn (45%) and anti (55%) isomers. Data for anti-isomer are shown. $^1$H NMR, ppm: 14.41 (1H, s, oxime group), 7.68 (2H, multiplet), 7.59 (1H, multiplet). $^{13}$C NMR, ppm. 135.26—carbons at 2,6-positions, 133.26—carbons at 3,5-positions, 129.07—carbon at 4-position, 127.27 carbon at I-position, 129.64—oxime carbon, 114.29—CN-group. UV-visible spectrum, $\lambda_{max}$ (EtOH)/nm, $\epsilon/(dm^3\ M^{-1}\ cm^{-1})$: 216 nm ($\epsilon$=15080 $M^{-1}\ cm^{-1}$), 269 nm shoulder. IR data, $cm^{-1}$: 3420$\nu$(O—H); 3171, 3083$\nu$(C—H); 2250$\nu$(C≡N); 1577, 1559$\nu$(C═C); 1431$\nu$(C═C)-Ph-group pulsing; 725, 783, 794$\delta$(C—H)—1,2,3-Ph-group pattern; 1411$\nu$(C═N); 1047$\nu$(N—O); 1126$^{as}$, 1083$^s\nu$(C—Cl). Block-type single crystals, suitable for x-ray analysis, were obtained during slow evaporation within 2 weeks of the ethyl ether/$CCl_4$ solvent mixture.

Use of Preferred Compositions as Enzyme Inhibitors

Human "carbonyl reductase" is believed to comprise several isoenzymes, which are members of the short-chain dehydrogenase/reductase superfamily and monomeric or tetrameric with subunit molecular weight of approximately 30 kDa. Carbonyl reductase uses NADPH, and may have physiological roles including quinone detoxification or other roles.

Multiple studies point to human carbonyl reductase (such as carbonyl reductase 1) having a role in the production of the anthracycline metabolites believed to cause cardiotoxic side effects in cancer patients either near the time of the chemotherapy or at some later time. This disease or condition of cardiotoxicity related to anthracycline drugs is briefly described above in the Related Art Section. Also, see FIG. 2 for one example of a mechanism of carbonyl reductase reduction of an anti-cancer anthracycline to a cardiotoxic alcohol metabolite. C13-hydroxy-metabolites are believed to be the principle cardiotoxic agents resulting from enzyme action upon anthracyclines.

In addition, because the anthracycline metabolite(s) are believed to not possess the anti-neoplastic properties of the parent anthracycline(s), carbonyl reductase may also contribute to anthracycline drug resistance. In other words, carbonyl reductase may lower anthracycline concentrations in the human body by catalyzing conversion of the anthracycline, and, hence, may lower the amount of cancer cells killed by a given dose of anthracycline drug.

The preferred compositions and methods comprise compounds that have at least one halogenated (or pseudo-halogenated) aryl/phenyl group, and, more preferably, halogenated arylcyanooximes. Several of these arylcyanooximes, that is, the C1, C2, C3, C4, C5, and C6 compounds described above, have been shown by the inventor to inhibit carbonyl reductase, and are envisioned to allow an increase in anthracycline chemotherapy by offsetting the negative side effects of this chemotherapy. Also, as discussed above, the preferred compositions and methods may decrease anthracycline drug resistance, further improving the results of anthracycline chemotherapy.

C1, C2, C3, C4, C5, and C6 have been shown by the inventor to be uncompetitive inhibitors against both coenzyme and carbonyl substrates, with $K_{ii}$ values in the low to mid micromolar range (10.8-72 μM). These preferred compounds have been seen to exhibit inhibition patterns suggestive of binding to multiple enzyme forms, which may mean that increased anthracycline dosages may not overcome the inhibition.

Cyanooximes—compounds with general formula HO—N═C(CN)—R(R=electron withdrawing group)—represent a new class of biologically active molecules that received attention because of their ability to bind different metal ions. See the documents following. Ciba Geigy AG. Srodek ochriny roslin przed dzialaniem agresywnych chemikalii rolniczych. Patent of Poland #127786, 1985; Ciba Geigy AG. Mittel zum Schutz von Kulturpflanzen von agressiven Herbiziden. Patent of Austria #367268, 1982; Skopenko, V. V.; Palii G. K.; Gerasimclhuk, N. N.; Makats, E. F.; Domashevskaya O. A.; Rakovskaya, R. V. Nitrosothiocarbamyl-cyamnethanid of potassium or sodium which show antimicrobial activity. Patent of the USSR #1405281, 1988; Davidson, S. H. 2-Cyano-2-hydroximinoacetamides as plant disease control agents. Patent of the U.S. Pat. No. 3,957,847, 1978; Kuhne, A.; Hubele, A. Method for the cultivation of plants employing α-cyanohydroximinoacetamide derivatives. Patent of the U.S. Pat. No. 4,063,921, 1978).

To the inventors' knowledge, however, the C1, C2, C3, C4, C5, and C6 arylcyanooximes reported herein have not been used in any process for improving efficacy of drugs used in cancer treatment of for treating or preventing side effects of cancer treatment or cardiotoxicity. Further, the synthetic methods for creation of C1, C2, C3, C4, C5, and C6 have not been previously reported. The inventors believe that said effective and safe doses may be found without undue experimentation by one of skill in the art after reading this disclosure.

In use, one or more of the preferred compounds (C1, C2, C3, C4, C5, and C6) may be used in a pharmaceutical composition, which may also comprise one or more of the anthracycline drugs and/or other chemotherapy drugs or other medicines that may be beneficial to the cancer patient. Preferably, the C1, C2, C3, C4, C5, and C6 and anthracycline compositions are given at levels that produce the desired anti-cancer effects without the cardiotoxicity side effects. Therefore, the relative compositions may be changed for different anthracyclines and/or for different patients and/or for different cancers. The methods include treatment of, or treatment of side effects, for all cancers for which anthracyclines are used. Embodiments of the invention therefore include a pharmaceutical composition comprising at least one anthracycline compound and C1, C2, C3, C4, C5, C6 or a mixture of some of all thereof. The inventor envisions that there may be analogs or derivatives of C1, C2, C3, C4, C5, and/or C6 that also may be effective in compositions and methods of the invention. For example, the compositions may include anthracycline compounds selected from the group consisting of adriamycin/doxorubicin, daunorubicin/daunomycin, epirubicin, idarubicin, and a mixture of two or more thereof.

While the preferred patients are humans, animals may also benefit from the compositions and methods. Embodiments of the invented method may be for preventing or treating cardiotoxicity associated with anthracycline cancer chemotherapy in a mammal in need thereof, wherein the method comprises administering to the mammal a composition comprising an effective amount of a pharmaceutical composition comprising at least one anthracycline compound and at least one compound or mixture selected from the group consisting of C1, C2, C3, C4, C5, C6, a mixture of some of all of C1, C2, C3, C4, C5, and/or C6, an analog and/or derivative of C1, C2, C3, C4, C5, C6, and mixtures of two or more thereof. Effective amounts will be determined by methods known to those of skill in the art, Examples of anthracycline compounds include adriamycin/doxorubicine), daunorubicin/daunomycin, epirubicin, idarubicin, and a mixture of two or more thereof.

Instead of, or in addition to, administering a pharmaceutical composition including both anthracycline(s) and C1, C2, C3, C4, C5, and/or C6, separate pharmaceutical compositions may be used. For example, methods may include preventing or treating a disease or condition associated with carbonyl reductase in a mammal in need thereof by administering to the mammal a first pharmaceutical composition comprising at least one anthracycline compound; and also administering to the mammal a second pharmaceutical composition comprising C1, C2, C3, C4, C5, or C6, or a mixture of some or all thereof. The first and second pharmaceutical compositions may be administered at the same time, or may be administered at nearly the same time (for example, within 15 minutes or less), or preferably within a few hours of each other (for example, within 2 hours or less). It may be beneficial to treat the patient with C1, C2, C3, C4, C5, and/or C6 prior to anthracycline therapy (for example, two hours or less prior to anthracycline treatment), to block carbonyl reductase before administration of the anthracycline drug(s).

Inhibition Data

Figure 5A:
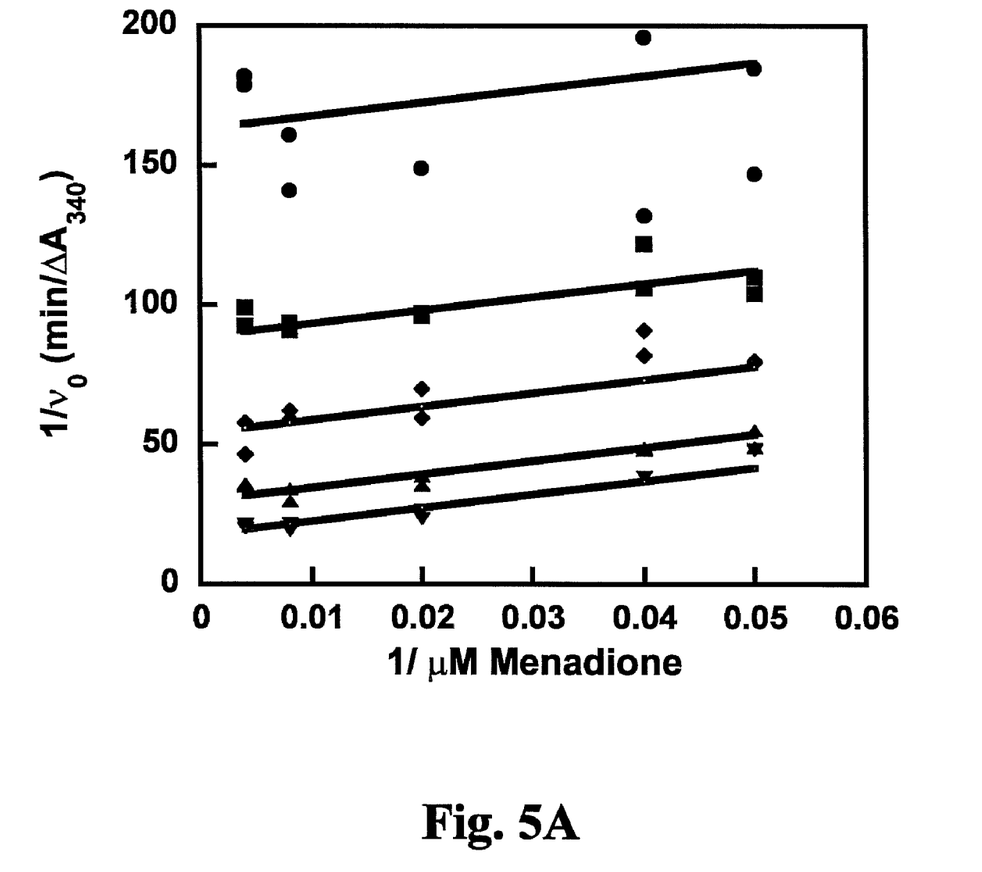
FIGS. 5A and B are graphs showing oximino(2,4-dichlorophenyl)acetonitrile (C5) as an uncompetitive inhibitor against both menadione (FIG. 5A) and NADPH (FIG. 5B).
Figure 5B:
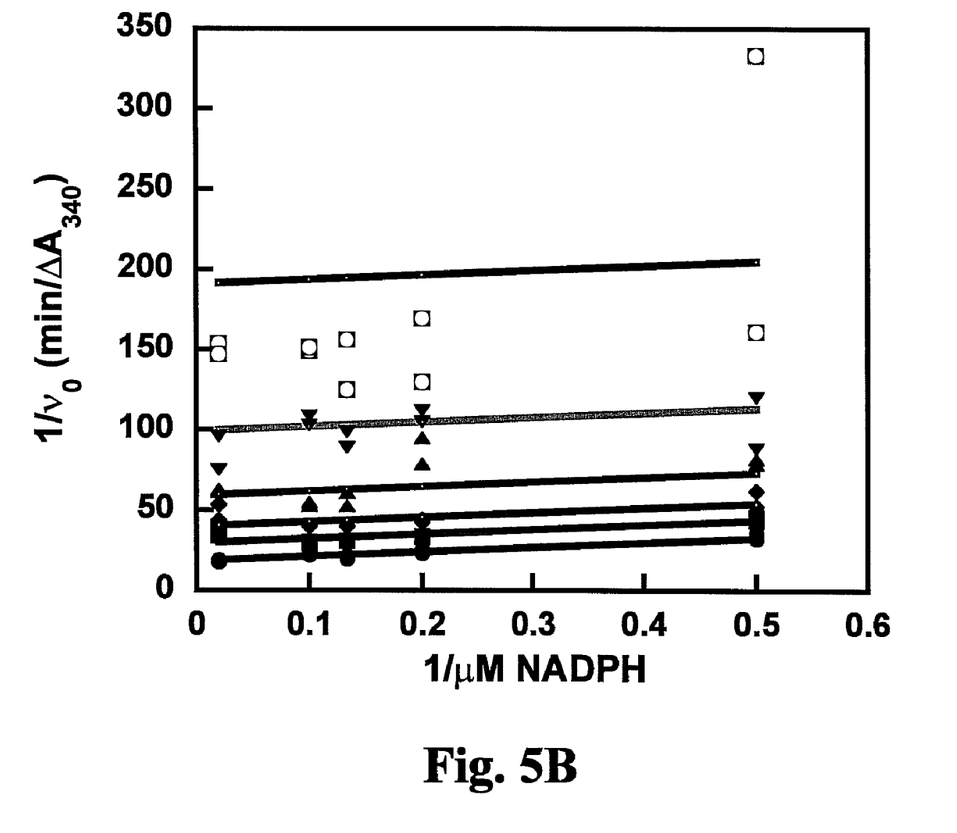
Figure 6:
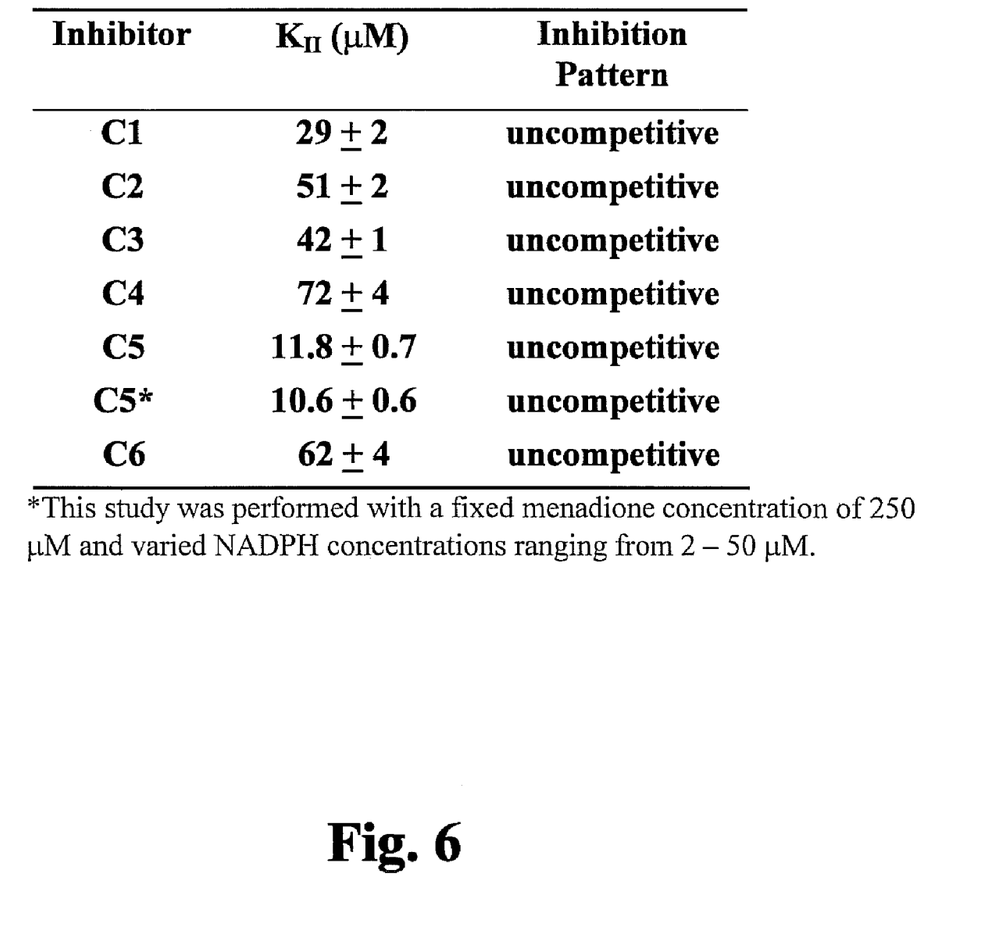
FIG. 6 describes inhibition patterns seen with inhibitors C1, C2, C3, C4, C5, and C6 wherein $K_{II}$ stands for the intercept inhibition constant.

Six arylcyanooximes (C1, C2, C3, C4, C5, and C6) were tested as possible inhibitors for carbonyl reductase. (See the syntheses described earlier in this disclosure). All were found to be uncompetitive inhibitors against the carbonyl substrate, but only C5 (oximino(2,4-dichlorophenyl)acetonitrile) was found to be a potent inhibitor of carbonyl reductase. See FIGS. 3A-F for the structures of the arylcyanooximes that were tested and found to be uncompetitive inhibitors. See FIGS. 5 A and B, portraying the 1/rate vs. 1/substrate concentration taken with C5, with menadione and NADPH as the varied substrates, respectively. As will be understood by those of skill in the art, the FIGS. 5A and B data show changes in only y-intercept, indicating uncompetitive inhibition. As illustrated in FIG. 6, all of the inhibitors tested showed uncompetitive inhibition. Therefore, while compositions comprising C5 are preferred, compositions comprising C1, C2, C3, C4, and/or C6 are also included in embodiments of the invention and are also expected by the inventors to be beneficial in the methods of the invention.

Figure 7:
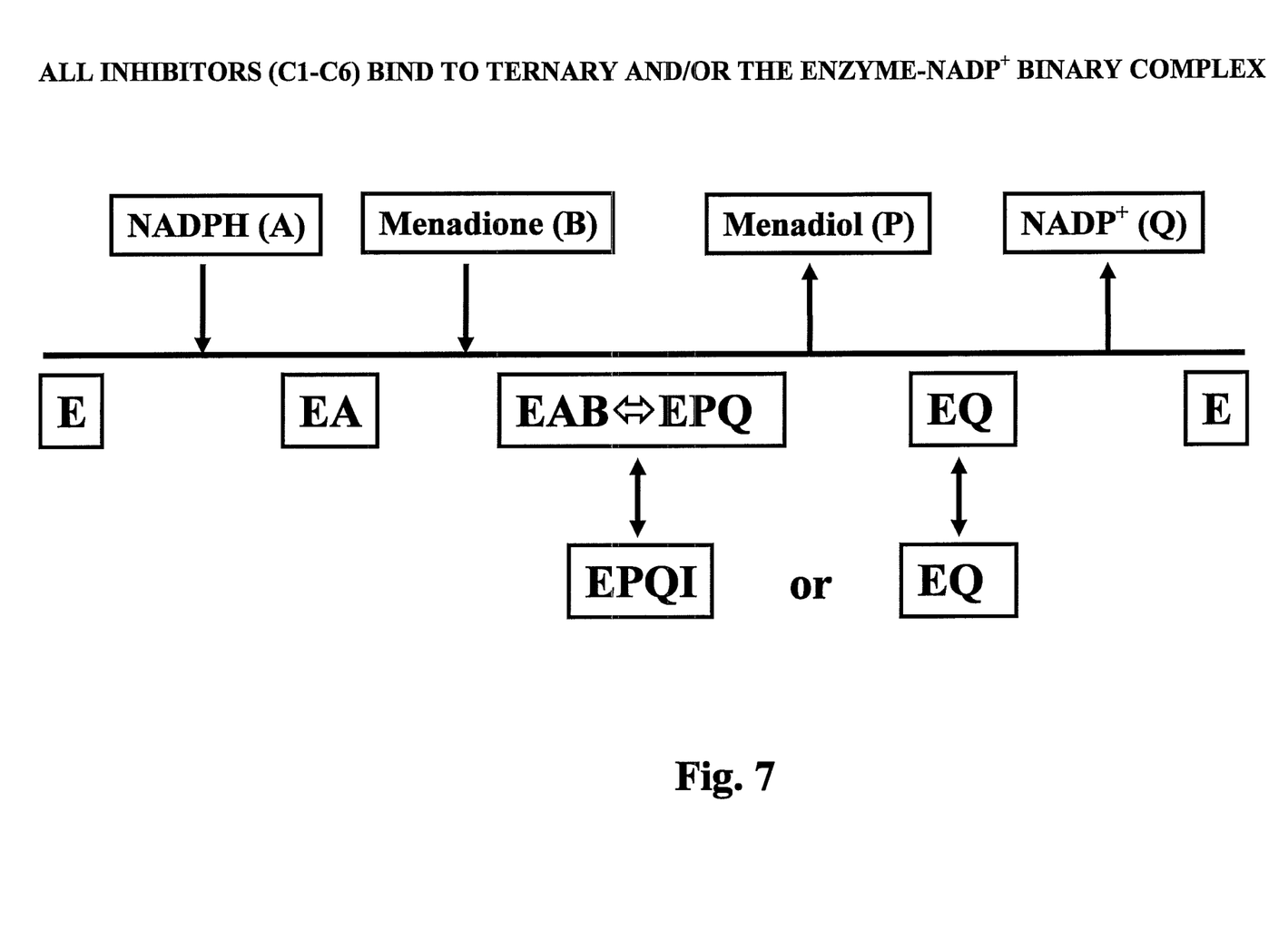
FIG. 7 summarizes data showing that all of the inhibitors bind to enzyme forms distinct from those to which NADPH and menadione bind, as determined from inhibition studies such as those represented in FIGS. 5A, 5B, and 6. All of the inhibitors C1, C2, C3, C4, C5, and C6 (represented by "I") bind to ternary and/or the enzyme-NADP+ binary complex. Enzyme (CR) is represented by "E". Menadione could be replaced by anthracyclines or other carbonyl-containing substrates.

From the above inhibition patterns, the inhibitors C1, C2, C3, C4, C5, and C6 more likely bind to the enzyme-NADP+ binary complex, or possibly the enzyme-menadione-NADPH ternary complex as illustrated in FIG. 7. It is expected that substrate carbonyls should not appreciably compete against the preferred inhibitors at these sites. Thus, said preferred inhibitors according to the invention are expected to remain available for, and will effectively carry out, inhibition of the mechanism that would otherwise result in lower efficacy of anthracycline(s) drugs and in cardiotoxic compounds.

Although this invention has been described above with reference to particular means, materials and embodiments, it is to be understood that the invention is not limited to these disclosed particulars, but extends instead to all equivalents within the broad scope of the following claims.

The invention claimed is:

1. A pharmaceutical composition for reducing cardiotoxicity during anthracycline cancer treatment, the composition comprising at least one anthracycline compound selected from the group consisting of adriamycin, daunomycin, daunorubicin, doxorubicin, epirubicin, idarubicin, and mixtures of two or more thereof, and at least one compound adapted to limit formation of anthracycline alcohol metabolite(s) and being a human carbonyl reductase enzyme inhibitor selected from the group consisting of: oximino(2,4-difluorophenyl)acetonitrile ("C1"), oximino(2,6-difluorophenyl)acetonitrile ("C2"), oximino(2,5-difluorophenyl)acetonitrile ("C3"), oximino(2-chloro-6-fluorophenyl)acetonitrile ("C4"), oximino(2,4-dichlorophenyl)acetonitrile ("C5"), oximino(2,6-dichlorophenyl)acetonitrile ("C6), and mixtures of two or more thereof, wherein the pharmaceutical composition comprises an amount of said anthracycline compound effective for cancer cell cytotoxicity, and the pharmaceutical composition comprises an amount of human carbonyl reductase enzyme inhibitor such that the concentration gives a $K_{ii}$ value in the range of 10.8-72 μM.

2. A composition as in claim 1 wherein said human carbonyl reductase enzyme inhibitor is made by nitrosating a substituted phenylacetonitrile by treatment with gaseous methylnitrite, $CH_3ONO$, at room temperature or below.

* * * * *

UNITED STATES PATENT AND TRADEMARK OFFICE
CERTIFICATE OF CORRECTION

PATENT NO. : 7,727,967 B2
APPLICATION NO. : 11/776536
DATED : June 1, 2010
INVENTOR(S) : Henry A. Charlier, Jr. and Nikolay Gerasimchuk It is certified that error appears in the above-identified patent and that said Letters Patent is hereby corrected as shown below:

On the Title Page
Name of the Assignee Item (73) should read: Boise State University
Assignee of the interest of Henry A. Charlier, Jr.

Signed and Sealed this
Tenth Day of April, 2012

David J. Kappos
*Director of the United States Patent and Trademark Office*